(12) United States Patent
Gonzales et al.

(10) Patent No.: US 8,157,788 B2
(45) Date of Patent: Apr. 17, 2012

(54) MULTI-SITE DRUG DELIVERY PLATFORM

(75) Inventors: Gilbert R. Gonzales, New York, NY (US); Paolo L. Manfredi, New York, NY (US)

(73) Assignee: Paolo L. Manfredi, New York, NY (US)

( * ) Notice: Subject to any disclaimer, the term of this patent is extended or adjusted under 35 U.S.C. 154(b) by 338 days.

(21) Appl. No.: 10/702,893

(22) Filed: Nov. 6, 2003

(65) Prior Publication Data
US 2005/0101936 A1 May 12, 2005

(51) Int. Cl.
*A61M 25/00* (2006.01)
*A61M 31/00* (2006.01)

(52) U.S. Cl. .......... 604/514; 604/285

(58) Field of Classification Search .......... 604/514, 604/517, 15, 516, 285, 288
See application file for complete search history.

(56) References Cited

U.S. PATENT DOCUMENTS

| | | | |
|---|---|---|---|
| 3,573,290 A * | 3/1971 | Sallmann et al. | 544/107 |
| 3,574,820 A | 4/1971 | Johnson et al. | |
| 4,028,467 A * | 6/1977 | Berger | 514/221 |
| 4,258,027 A * | 3/1981 | Ullman et al. | 424/467 |
| 4,339,442 A * | 7/1982 | Takemoto et al. | 514/26 |
| 4,405,597 A | 9/1983 | Takagishi et al. | |
| 4,409,212 A * | 10/1983 | Mondadori | 514/217 |
| 5,073,641 A * | 12/1991 | Bundgaard et al. | 560/56 |
| 5,472,704 A * | 12/1995 | Santus et al. | 424/435 |
| 5,492,937 A | 2/1996 | Bogentoft et al. | |
| 5,635,210 A * | 6/1997 | Allen et al. | 424/465 |
| 5,662,921 A | 9/1997 | Fein et al. | |
| 5,719,122 A | 2/1998 | Chiodini et al. | |
| 6,161,260 A * | 12/2000 | Flewitt | D24/101 |
| 6,262,098 B1 * | 7/2001 | Huebner et al. | 514/378 |
| 6,264,626 B1 * | 7/2001 | Linares et al. | 604/15 |
| 6,375,963 B1 | 4/2002 | Repka et al. | |
| 7,077,826 B1 * | 7/2006 | Gray | 604/171 |
| 7,544,371 B2 * | 6/2009 | Kunzler et al. | 424/484 |
| 2001/0000470 A1 | 4/2001 | Bernstein et al. | |
| 2002/0132850 A1 * | 9/2002 | Bartholomaeus et al. | 514/567 |
| 2002/0161016 A1 * | 10/2002 | Tam et al. | 514/278 |
| 2003/0003152 A1 * | 1/2003 | Ream et al. | 424/479 |
| 2003/0108705 A1 * | 6/2003 | Duffield et al. | 428/36.6 |
| 2003/0170296 A1 * | 9/2003 | Sintov et al. | 424/449 |
| 2003/0219479 A1 * | 11/2003 | Chen et al. | 424/466 |
| 2004/0180916 A1 * | 9/2004 | Levine | 514/282 |
| 2004/0253310 A1 * | 12/2004 | Fischer et al. | 424/472 |

FOREIGN PATENT DOCUMENTS

| | | |
|---|---|---|
| GB | 2 314 024 A | 12/1997 |
| WO | 90/03776 | 4/1990 |
| WO | 91/03099 | 3/1991 |
| WO | 01/89473 A1 | 11/2001 |

* cited by examiner

*Primary Examiner* — Jackie Ho
*Assistant Examiner* — Andrew Gilbert
(74) *Attorney, Agent, or Firm* — Wood Herron & Evans LLP

(57) ABSTRACT

A pharmaceutical composition for administration to a patient body. The composition includes a physiologically-acceptable formulation including at least one active pharmaceutical ingredient, wherein said physiologically-acceptable formulation including said at least one active pharmaceutical ingredient is provided in a delivery form, said delivery form being administrable to a patient body through a plurality of administration routes, which include the oral and rectal routes.

27 Claims, 2 Drawing Sheets

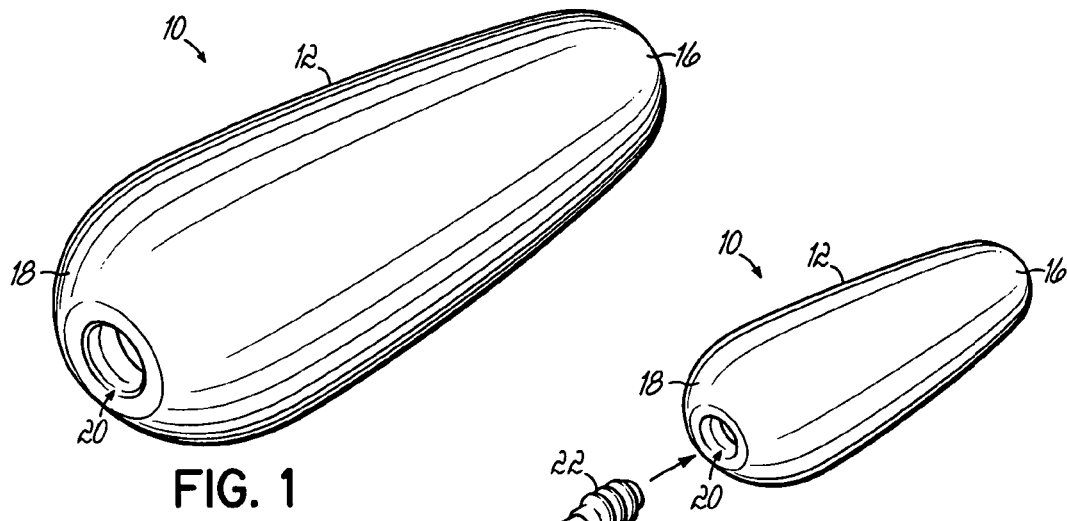
FIG. 1
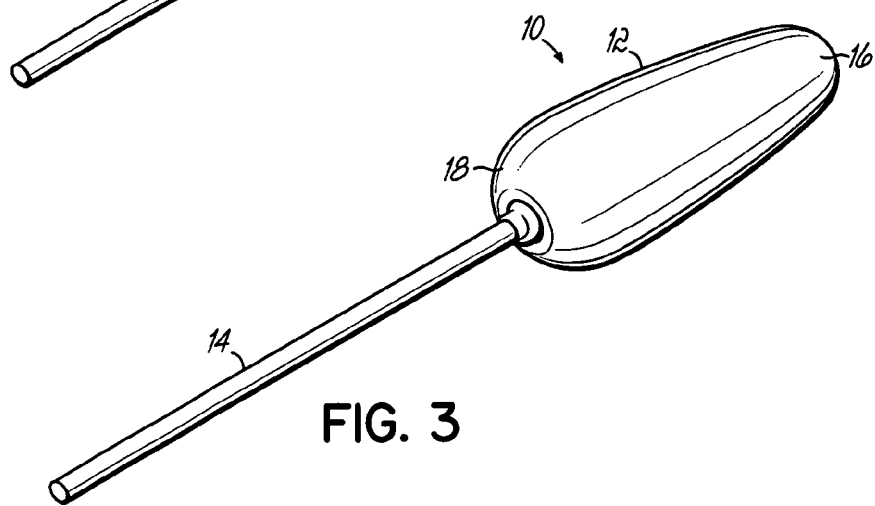
FIG. 2
FIG. 3
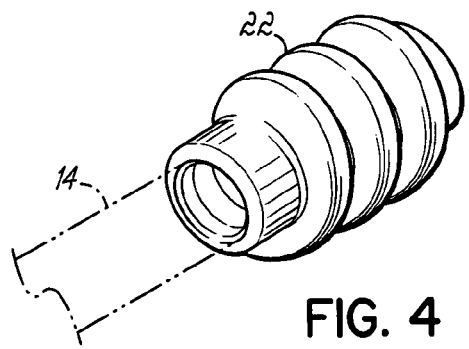
FIG. 4

MULTI-SITE DRUG DELIVERY PLATFORM

FIELD OF THE INVENTION

The present invention relates generally to drugs and drug delivery systems, and specifically to drugs and drug delivery systems designed to be delivered via multiple alternate delivery sites.

BACKGROUND OF THE INVENTION

Non-parenteral drugs, which are found in delivery forms such as tablets, suspensions, suppositories, etc., are generally adapted to be administered to a patient via a single delivery site or administration route. For example, a chewable tablet is designed to be administered solely through the oral cavity, and its particular formulation is adapted to be delivered in that particular manner. Should a particular drug require administration through an alternate administration route, such as a suppository, which is delivered via the rectum, a different formulation including the drug will be used. There are several drawbacks which result from delivery forms of drugs which only allow administration of a particular formula to a patient via a single delivery site or administration route.

One such drawback concerns situations in which it may become difficult or impossible to administer a medication via a particular administration route. As a first example, one patient group in which this drawback may be prevalent is composed of children. Many medications are dispensed as tablets or other forms designed to be taken orally, such as suspensions. However, sick children have a propensity to become "cranky", especially when ill, and thus become adverse to oral intake of medications. When this happens, medication may not be taken in the correct amounts, at the correct time, or taken at all, and compliance with the medicinal regimen suffers. Without proper compliance, the health of the child may worsen. This only compounds the problem in that many sick children often become even less cooperative as symptoms of the disease or sickness become more intense.

As a result of this drawback, a preparation that can be rectally administered as a suppository may allow the medicinal regimen to be followed, thus resolving the health problems of the child and resolving a potential emotionally charged family crisis by providing the medication in a delivery form that can be administered in the event that delivery via the oral route is unlikely or impossible.

However, current rectal suppositories, including pharmaceutical ingredients, are prepared in a delivery formulation that differs from the formulation used for a delivery form adapted for oral administration Thus, the oral tablet, gel, etc. cannot be administered rectally. Thus, in order to resolve the problem of the uncooperative patient, two different forms of the same medication, one oral and one rectal, need to be kept on-hand. Such a solution is impractical and generates unnecessary costs from the standpoint of the producer, who must generate pharmaceutical compositions in two separate delivery forms, and the customer, who must purchase pharmaceutical compositions in two separate delivery forms.

A second example of compliance problems may arise when the intrinsic nature of many severe health problems that commonly affect patients makes swallowing problematic. For example, gastrointestinal diseases, which involve nausea and vomiting; asthma, which involves gasping for air; seizures, which involve a change in mental status; and pharyngitis and other illnesses, which involve a severe sore throat, are examples of conditions and symptoms that oftentimes make it desirable to have a medication that is deliverable by a route other than the oral cavity. Even the most cooperative patients, those who desire to take oral medications, oftentimes cannot swallow pills, tablets, etc. when suffering from nausea and vomiting, when gasping for air from an asthma attack, when incapacitated during a seizure, or when troubled by severe sore throat.

As a third example, certain situations may require urgent or emergent delivery of medication. In such situations, it may be the case that a particular delivery form is impractical or impossible to be delivered. For example, it may be impossible to administer an oral delivery form of a composition to an incapacitated individual. Such an individual may require an alternative delivery form. In such cases, having the incorrect delivery form of a medication on hand can have grave, and possibly even fatal, consequences.

Thus, for both acutely ill patients and patients chronically dependent on medications, it is apparent that a drug delivery may be preferable via one administration route at one time, and at another time may be preferable or required via a different administration route, even as applied to the same disease and even during the same course of the same day. Thus, to eliminate the above drawbacks in current drugs and drug regimens, it would be desirable to develop a drug composition which allows for administration in different sites of a patient in order to allow a medication regimen to be complied with when one particular administration route is unavailable. Further, it would be desirable to provide a drug in a delivery form that allows one prescription to be written and filled without varying formulations. Still further, it would be desirable to allow for the prompt resolution of emergencies by providing a single delivery form which can be administered regardless of the status of the patient.

SUMMARY OF THE INVENTION

The present invention overcomes the drawbacks as described above in the Background of the Invention. It does so by providing a pharmaceutical composition for administration to a patient body that includes a physiologically acceptable formulation having an active pharmaceutical ingredient, wherein the formulation is provided in a single delivery form which may be administered to a patient through a plurality of administration routes. By providing a formulation in a single delivery form administrable by alternate routes, the present invention allows for a medication regimen to be complied with when one particular administration route is unavailable. Further, the present invention allows one prescription to be written and filled without varying the formulation of the composition. Still further, the present invention provides a composition that can be administered quickly, regardless of the age or status of the patient, or the symptoms exhibited by the patient.

The present invention thus includes multiple delivery forms devised to allow administration of physiologically acceptable biologically-active substances, with each delivery form deliverable to a patient body via a plurality of administration routes. These delivery forms may include solid and nonsolid forms. The administration routes used with these delivery forms may include oral transmucosal, rectal mucosal, and oral via the gastrointestinal tract. When the drug delivery form is solid, the present invention may include a physiologically acceptable biologically-active composition in the form of a lozenge on a handle in a lollipop or sucker form for transmucosal and/or gastrointestinal absorption, a lozenge off of a handle for transmucosal and/or gastrointestinal oral absorption, a swallowable tablet, a chewable tablet, or a dissolvable tablet for gastrointestinal absorption, a capsule including a softgel capsule, and a rectal suppository for rectal absorption. When the delivery form is nonsolid, administration routes may include oral, via the gastrointestinal tract or the oral mucosa, and rectal administration. The non-solid delivery form may include a physiologically acceptable biologically-active composition as a gel, liquid, paste, or foam. These non-solid preparations may be enclosed in a capsule including a softgel capsule that can be administered both orally and rectally, for oral transmucosal and gastrointestinal and/or rectal absorption. The non-solid delivery form may be applied via an applicator whether administered orally or rectally. The solid delivery form, including capsule and softgel capsule, may also be applied via an applicator whether administered orally or rectally. The composition in the delivery forms of the present invention may be used with both short-acting and long-acting drug preparations.

As a result, urgent and emergent health problems, seizures, asthma attacks, and dehydration from vomiting, can be resolved by delivery forms of the composition of the present invention. For example, diazepam, aminophylline, and/or promethazine may be administered rectally or alternatively orally with a transmucosal lollipop delivery form or a chewable or swallowable tablet or capsule that can also be used as a suppository. As described above, in urgent and emergent situations, the time lost in search for the right delivery form can have grave and even fatal consequences. By the present invention, a particular formulation can be immediately adapted to the needed delivery form. Further, the same tablet can be used either orally or rectally. Previously rectal administrations required a different formulation than a form for oral administration.

By providing formulations in a delivery form that are suitable for administration by a plurality of administration routes, the composition of the present invention may also result in significant cost savings. For example, such savings may be generated both directly through the lower cost of having one formula in a single delivery form versus the higher cost of several formulations of the same drug in different delivery forms, and indirectly, for example, in reducing the loss of time to parents and guardians and the costs associated with calls to doctors, trips back and forth for visits to doctors and pharmacists, etc. Significant costs associated with the healthcare system may also be cut significantly. For example, the time spent by pharmacists in preparing different delivery forms of drugs may be significantly reduced. Furthermore, a doctor may be able to write a single prescription for a drug that can then be used in different ways.

The benefits of the composition of the present invention may be especially pronounced in certain patients, such as children. As discussed above, it is well known that sick children are less than attentive to their medication regimen. Children oftentimes will easily refuse medications unless the formulation suits them at that particular moment. At one time a sick child may agree to an oral medication, but at another time, he or she may reject even the idea of taking a pill. Further, certain situations may arise where any patient, whether child or adult, is unwilling or unable to take a medication in a certain delivery form. Being able to switch easily from one route of administration to another allows the drug delivery systems of the present invention to resolve otherwise critical situations. The composition in the delivery forms of the present invention thus resolves the drawbacks described above in the background of the invention.

BRIEF DESCRIPTION OF THE DRAWINGS

The accompanying drawings, which are incorporated in and constitute a part of the specification, illustrate embodiments of the invention and, together with a general description of the invention given above, and the detailed description of the embodiments given below, serve to explain the principles of the invention.

FIG. 1 is a perspective view of a pharmaceutical composition in a delivery form, adapted to be delivered as a suppository or a tablet;

FIG. 2 is a perspective view of the pharmaceutical composition of the delivery form of FIG. 1 and a handle in order to further adapt the composition for oral administration as a lollipop to allow transmucosal and/or gastrointestinal absorption;

FIG. 3 is a perspective view of the pharmaceutical composition and handle of FIG. 2 as operatively connected for oral administration of the pharmaceutical composition;

FIG. 4 is a perspective view of the threaded tip of the handle as depicted in FIG. 2;

DETAILED DESCRIPTION OF THE INVENTION

Figure 5:
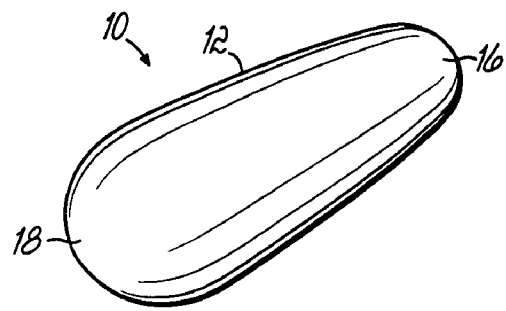
FIG. 5 is a perspective view of an alternate embodiment of a pharmaceutical composition in a delivery form, adapted to be delivered as a suppository or a tablet.

The present invention provides a composition for administration to a patient body that includes a physiologically acceptable formulation having an active pharmaceutical ingredient, wherein the formulation is provided in a delivery form which may be administered to a patient through a plurality of administration routes. It also provides a method of administering the composition to a patient by alternative administration routes.

In one embodiment of the present invention, the administration route via which the composition may be administered to a patient may be an oral administration route. The oral administration route for absorption of the active pharmaceutical ingredient of the formulation may be transmucosal or gastrointestinal. For example, when the route of administration is oral transmucosal, the composition may be adapted for absorption across the buccal, sublingual, and/or gingival mucosa. In an alternate embodiment, the administration route may be a rectal administration route, and more particularly, a rectal transmucosal route. It will be apparent to those of skill in the art that while the administration routes may include oral and rectal, they are not limited to oral and rectal routes. As will be recognized by those having skill in the relevant art, the administration routes may include any route suitable for any delivery form of the composition of the present invention.

Further, the composition of the present invention may include a delivery form that is either solid or non-solid. All drugs that are available in suppository form may be used in the solid delivery form of the present invention. All drugs that are available in an oral liquid form may be used in the non-solid delivery form of the present invention. Non-solid delivery forms may include those that are semi-solid, such as a gel. Further, the drug delivery forms of the present invention are adaptable to all drugs that can be fitted in a capsule including a softgel capsule. Further, the drug delivery forms of the present invention are adaptable to all drugs that are suitable for both oral and rectal use.

When the delivery form of the composition of the present invention is a solid delivery form, such delivery form may include a suppository, a lozenge, a swallowable tablet, a chewable tablet, a dissolvable tablet, or a capsule. Such a solid delivery form is shown in FIG. 1. Those having skill in the art will recognize that the list of solid delivery forms above is merely exemplary, and that any solid delivery form that is administrable to a patient may be suitable for use in the present invention. In use, solid delivery forms, such as those described above, may be administered orally. For example, forms such as the tablet forms described above, may be taken by swallowing the tablet or capsule whole, chewing the tablet, or allowing the tablet to dissolve either prior to or during administration to the oral cavity. A lozenge form may be swallowed, chewed, or dissolved in the mouth, or may be attached to a handle to be administered as a lollipop, as will be described further below. If the solid delivery form, as described above, cannot or will not be taken orally, it may be administered rectally, without any need for altering the formulation of the composition.

Tablets can be manufactured by direct compression, wet granulation, or any other technique used in the manufacture of tablets. Capsule can be manufactured by any technique used in the manufacture of capsule, including softgel capsules.

Referring now to FIGS. 1-4, an example of a solid delivery form 12 as a suppository is shown, and as it may be adapted for use as a chewable tablet, swallowable tablet, dissolvable tablet, lozenge, or lollipop. For example, the composition 10 in a particular formulation including an active pharmaceutical ingredient may have a solid delivery form 12 of a suppository, as is shown in FIG. 1. However, a particular patient, such as a child, may not be readily induced to take medication in the form of a suppository. However, the child may be much more amenable to taking the medication in the form of a lollipop. Thus, in one embodiment, the delivery form 12 may be adapted to include a handle 14, the handle 14 being adapted to be operatively connected to the solid delivery form 12. In the illustrated embodiment, the suppository includes a proximal end 16 and a distal end 18. The distal end 18 defines a central bore 20 which is adapted to receive a handle 14. When the handle 14 is not in receiving relationship with the bore 20, the composition 10 may be administered as a suppository, lozenge, or tablet. When the handle 14 is in receiving relationship with the bore 20, as is seen most readily in FIG. 3, the composition 10 in this delivery form 12 may be used as a lollipop. In order to facilitate this adaptation, the handle 14 may be threaded, as seen in FIG. 4 (at reference numeral 22), in order that it may be received by the bore 20, as shown by FIGS. 2 and 3.

Figure 6:
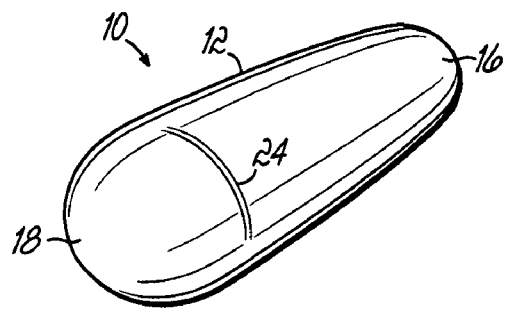
FIG. 6 is a perspective view of a pharmaceutical composition in a delivery form, adapted to be delivered as a suppository or a tablet, and including a score line.

As described briefly above, there are several various embodiments of the solid delivery form that may be adapted for administration to a patient through various administration sites in a patient body. Such embodiments include, but are not limited to, a lollipop (lozenge on a handle), a troche or lozenge (off a handle), a suppository (off a handle), a dissolvable tablet (off a handle), a swallowable tablet (off a handle), and a chewable tablet (on or off a handle). In one particular embodiment of the solid delivery form of the present invention, the composition may include an oval, flat base with rounded edges as a tablet form. This tablet, as can be seen in FIGS. 1-4, may define a threaded passageway so that the tablet may be adapted to being connected to a complementarily threaded handle. It will be recognized by those of skill in the art that other shapes, other than that described above, may be possible in a solid delivery form, while remaining consistent with the principles of the present invention. For example, such embodiments may include a handleless delivery form having no bore or threaded handle (i.e., a chewable, swallowable, and suppository form without unit boring or a threaded handle, as can be seen in FIGS. 5 and 6).

As described above, the delivery form of the composition of the present invention may also include non-solid delivery forms. When a non-solid delivery form is selected, the delivery form may include, but is not limited to, a gel, a liquid, a paste, and a foam. A non-solid delivery form may be preferable at times because there are certain situations wherein a non-solid delivery form may be more suitable than a solid delivery form. These include (1) use with younger children who have difficulty with solid formulations, (2) use for drugs having a poor palatability—taste-masking is easier with liquid formulations—and (3) use with drugs that require higher doses, since it is easier to provide higher concentrations of active pharmaceutical ingredients in non-solid forms.

When presented as a gel, paste, or foam, the non-solid delivery form is also a semi-solid. In such form, the active pharmaceutical ingredient may be combined with other components, such as excipients, that are selected and admixed with the active pharmaceutical ingredient or ingredients to give a delivery form of the desired consistency, by methods well know to those of skill in the art. When presented as a non-solid liquid, the delivery form may be presented as a suspension, solution, or an aerosol form, or other liquid delivery form. Such a form may typically include a solution or suspension of the active pharmaceutical ingredient or ingredients in a physiologically acceptable aqueous solvent. A liquid suspension may be administrable orally or rectally. An aerosol formulation may be administrable orally or nasally. It will be recognized by those having skill in the art that the delivery forms and administration routes discussed above are exemplary and that the non-solid delivery forms may be administrable to a patient via any suitable route.

In order to facilitate administration of the non-solid delivery form, there may further be provided an applicator which includes a delivery component. This delivery component may be a plunger, or a squeezable housing or body, for example. It will be recognized by those of skill in the art that any structure that facilitates delivery of the non-solid delivery form may be used as the delivery component of this embodiment of the present invention.

Figure 7:
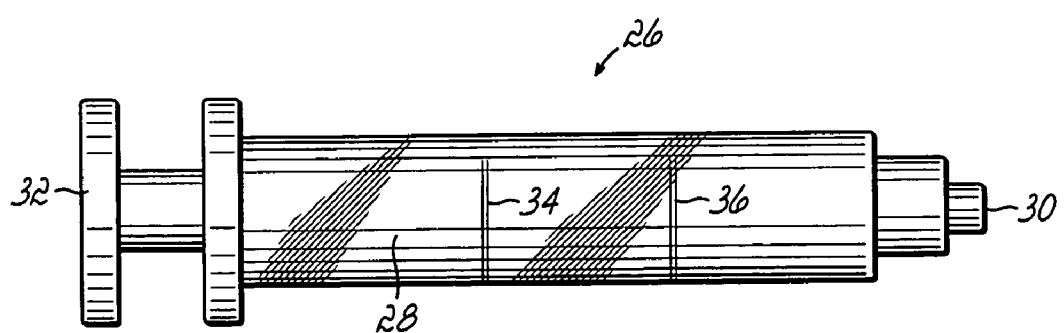
FIG. 7 is a perspective view of an applicator used to delivery a non-solid delivery form of the pharmaceutical composition of the present invention.

Referring now to FIG. 7, one particular embodiment in a non-solid delivery form is shown. The applicator in this embodiment may be a syringe 26 having a barrel 28, a distal tip 30 and a plunger 32. The composition, in a non-solid form, is contained within the barrel 28 prior to use. By depressing the plunger 32, the composition may exit the barrel 28 through the tip 30 to be dispensed to a patient through one of multiple administration routes, such as oral or rectal. The syringe may include first and second dosage lines 34, 36. These may be used to determine differing dosages to be given depending on the route of administration. For example, when administering the composition rectally, one may depress the plunger 32 up to the first dosage line 34. However, when administering the composition orally, one may depress the plunger 32 up to the second dosage line 36.

As described above, the formulation of the composition includes an active pharmaceutical ingredient. This active pharmaceutical ingredient may be selected from analgesics, anti-allergy medications, anti-asthma medications, antibiotics, antiviral drugs, antifungal drugs, anticholinergics, anticonvulsants, antidepressants, antihistamines, antiemetics, antiseizure, antispasmodics, aminophylline, ascorbic acid, aspirin, acetaminophen, barbiturates, benzodiazepines, bisacodyl, butyrophenones, caffeine, chloral hydrate, chlorpromazine, clindamycin, clotrimazole, codeine, corticosteroids, dextromethorphan, diazepam, dinoprostone, diphenhydramine, ergotamine, estrogens, fentanyl, ferrous sulfate, guaifenesin, haloperidol, hormonal supplements, hydromorphone, indomethacin, kaolin, pectin, laxatives, lithium, loperamide, meclizine, meprobamate, methadone, metronidazole, miconazole, morphine, NSAIDS, opioids, orphenadrine, oxymorphone, pentobarbital, phenobarbital, phenothiazines, phenyloin, prochlorperazine, progestins, promethazine, ritalin, simethicone, spiramycin, sulfonamides, theophylline, trimethobenzamide, valproic acid, and vitamins. It will be recognized by those having skill in the art that the preceding list of active pharmaceutical ingredients is merely exemplary, and that any active pharmaceutical ingredient that is suitable to be combined into a composition in a delivery form as described herein may be used in the formulation of the composition of the present invention. It will further be recognized by those of skill in the art that it is not necessary that only one active pharmaceutical ingredient be included in the composition of the present invention, but that a plurality of active pharmaceutical ingredients may be included in the composition.

As described previously, the composition of the present invention may include components other than the active pharmaceutical ingredient. These components may include a base present in the formulation to cause the formulation to be suitable for both oral and rectal applications. In particular embodiments, this base may be selected from glycerinated gelatin, polyethylene glycol, and MBK fatty acid.

The components of the composition may also include at least one additive, and generally a plurality of additives, used to maximize palatability of the composition, in terms of characteristics such as taste-masking, texture and color. These additives include, but are not limited to, flavoring agents, coloring agents, sweetening agents, preservatives, adhesive-promoting agents, and glidants.

The components of the composition may further include at least one excipient. Such an excipient may be used for various purposes, such as to facilitate tableting, or to facilitate the dissolution of the delivery form in the mouth. This at least one excipient may be selected from the group consisting of mannitol, dextrose, lactose, sucrose, and calcium carbonate.

With certain active pharmaceutical ingredients, absorption of the ingredient into the patient body may occur more rapidly and/or completely through rectal absorption than through gastrointestinal or oral transmucosal absorption. For example, methadone may exhibit up to about 80-100% absorption when administered rectally (J. S. Morley, *New Perspectives in Our Use of Opioids*, Pain Forum, 8:4 (1999), 200-205; E. Bruera, et al., *Methadone Use in Cancer Patients with Pain: A Review*, J. Palliative Medicine, 5 (2002) 127-138; C. Ripamonti, et al., *Switching from Morphine to Oral Methadone in Treating Cancer Pain: What is an Equianalgesic Dose Ration?*, Journal of Clinical Oncology, 16:10 (1998), 3216-3218), whereas the same active pharmaceutical ingredient may exhibit substantially less than about 60-80% absorption into the patient body when administered orally (J. S. Morley, *New Perspectives in Our Use of Opioids*, Pain Forum, 8:4 (1999), 200-205; E. Bruera, et al., *Methadone Use in Cancer Patients with Pain: A Review*, J. Palliative Medicine, 5 (2002) 127-138; C. Ripamonti, et al., *Switching from Morphine to Oral Methadone in Treating Cancer Pain: What is an Equianalgesic Dose Ration?*, Journal of Clinical Oncology, 16:10 (1998), 3216-3218). As described above, a particular delivery form, such as a tablet, may be administrable either orally or rectally, without having to obtain a different formulation of the composition. Thus, the concentration of active pharmaceutical ingredient administered will be the same, regardless of whether the composition is administered orally or rectally. However, due to the differing absorption rates of some ingredients, such as methadone, based on the administration route selected, it may be desirable in some circumstances to alter the delivery form to result in equal amounts of active pharmaceutical ingredient being absorbed regardless of the route of administration.

Thus, in one embodiment of the composition having a solid delivery form 12, such as a tablet as shown in FIG. 6, the tablet is provided with a score line 24. This score line 24 may be provided in the surface of the tablet, or other solid delivery form 12. The location of the score line 24 on the tablet may be reflective of the rates of absorption of the active pharmaceutical ingredient in the gut or rectum of a patient. For example, if a particular composition includes an active pharmaceutical ingredient of methadone, and that ingredient exhibits 100% absorption when taken rectally, but only 75% absorption when taken orally, then the tablet may include a score line that causes the tablet to break unevenly into two portions, one of those portions being 75% of the original tablet. Referring again to the Figures, it can be seen that the tablet of one embodiment of the present invention includes a distal end 18 and a proximal end 16. In the example described above then, the tablet would have a score line 24 located on the tablet, 75% of the total length of the tablet from the proximal, suppository insertion end 16. If 100% absorption were needed to effect a therapeutic result, the entire tablet would be administered orally, should that be the administration route of choice. However, if the composition were to be administered rectally, then the tablet would be first broken along the score line, and the portion exhibiting 75% of the total size of the original tablet would be administered rectally.

As a separate example, if a particular composition includes an active pharmaceutical ingredient of acetaminophen, because higher plasma levels of drug are achieved after oral doses compared to rectal does, there may be the need for a larger rectal dose compared to the oral dose. If 100% absorption were needed to effect a therapeutic result, the entire tablet-suppository containing acetaminophen would be administered rectally, should that be the administration route of choice. However, if the composition were to be administered orally, then the tablet-suppository would be first broken along the score line, and the portion exhibiting 75% of the total size of the original tablet would be administered orally.

The present invention also provides a method of administering the composition to a patient. This method includes providing a composition for administration to a patient body that includes a physiologically acceptable formulation having an active pharmaceutical ingredient, wherein the formulation is provided in a delivery form which may be administered to a patient body through a plurality of administration routes. The method further includes selecting at least a first or a second administration route, and delivering the composition in a delivery form to the patient via either the first administration route or the second administration route. A first administration route that may be selected includes oral administration. A second administration route that may be selected includes rectal administration. As described above, the administration route to be selected may be dependent on various factors, including, but not limited to, the age of the patient, the symptoms of the patient, and the status of the patient (i.e., whether the patient is incapacitated).

As described above, when administering the composition of the present invention to a patient body, the delivery form may be adapted for delivery, such as by operatively connecting a handle to a solid delivery form, or by breaking a solid delivery form along a score line disposed in the surface of the delivery form.

The principles of the present invention will be more apparent with reference to the following Examples.

EXAMPLES

Example 1

Promethazine

The following example includes the amounts of ingredients in a solid delivery form adapted to be used as a suppository in various mold sizes, which allows for various potencies for administration to differing ages of patients. A delivery form produced in a 1.3 Gm mold is suitable for children aged 3-6 years. A delivery form produced in a 2.0 Gm mold is suitable for children aged 6-12 years. And a delivery form produced in a 2.3 Gm mold is suitable for adults. Each delivery form is prepared for use as a suppository. However, in the event the medication cannot be taken rectally, the medication may be taken orally alternatively. The various amounts of ingredients are as follows:

| Promethazine 12.5 mg/1.3 Gm mold | |
|---|---|
| Promethazine | 12.50 mg |
| Stevia Powder | 2.00 mg |
| Silica Gel | 1.30 mg |
| MBK Fatty Base | 1.285 gms |
| Flavor/Orange Conc. | 0.13 ml |
| Promethazine 12.5 mg/2.0 Gm mold | |
| Promethazine | 25.00 mg |
| Stevia Powder | 3.00 mg |
| Silica Gel | 2.00 mg |
| MBK Fatty Base | 1.970 gms |
| Flavor/Orange Conc. | 0.23 ml |
| Promethazine 12.5 mg/2.3 Gm mold | |
| Promethazine | 50.00 mg |
| Stevia Powder | 3.50 mg |
| Silica Gel | 2.30 mg |
| MBK Fatty Base | 2.244 gms |
| Flavor/Orange Conc. | 0.26 ml |

Example 2

Acetaminophen

The following example includes the amounts of ingredients in a solid delivery form adapted to be used as a suppository in various mold sizes, which allows for various potencies for administration to differing ages of patients. A delivery form produced in a 1.3 Gm mold is suitable for children aged 3-6 years. A delivery form produced in a 2.0 Gm mold is suitable for children aged 6-12 years. And a delivery form produced in a 2.3 Gm mold is suitable for adults. Each delivery form is prepared for use as a suppository. However, in the event the medication cannot be taken rectally, the medication may be taken orally alternatively. The various amounts of ingredients are as follows:

| Acetaminophen 120 mg/1.3 Gm mold | |
|---|---|
| Acetaminophen | 120.00 mg |
| Stevia Powder | 2.00 mg |
| MBK Fatty Base | 1.178 gms |
| Flavor/Orange Conc. | 0.13 ml |
| Acetaminophen 350 mg/2.0 Gm mold | |
| Acetaminophen | 350.00 mg |
| Stevia Powder | 3.00 mg |
| MBK Fatty Base | 1.672 gms |
| Flavor/Orange Conc. | 0.23 ml |
| Acetaminophen 750 mg/2.3 Gm mold | |
| Acetaminophen | 750.00 mg |
| Stevia Powder | 3.50 mg |
| MBK Fatty Base | 2.547 gms |
| Flavor/Orange Conc. | 0.26 ml |

Example 3

Acetaminophen; Codeine

The following example includes the amounts of ingredients in a solid delivery form adapted to be used as a suppository in various mold sizes, which allows for various potencies for administration to differing ages of patients. A delivery form produced in a 1.3 Gm mold is suitable for children aged 3-6 years. Each delivery form is prepared for use as a suppository. However, in the event the medication cannot be taken rectally, the medication may be taken orally alternatively. The various amounts of ingredients are as follows:

| Acetaminophen 120 mg, Codeine 12.5 mg/2.3 Gm mold | |
|---|---|
| Acetaminophen | 120.00 mg |
| Codeine | 12.50 mg |
| Stevia Powder | 2.40 mg |
| MBK Fatty Base | 1.165 gms |
| Flavor/Orange Conc. | 0.13 ml |

While the present invention has been disclosed by reference to the details of preferred embodiments of the invention, it is to be understood that the disclosure is intended as an illustrative rather than in a limiting sense, as it is contemplated that modifications will readily occur to those skilled in the art, within the spirit of the invention and the scope of the amended claims.

What is claimed is:

1. A pharmaceutical composition for administration to a patient body, comprising:
   a physiologically acceptable formulation including at least one active pharmaceutical ingredient;
   wherein said physiologically-acceptable formulation including said at least one active pharmaceutical ingredient is provided as a single solid delivery form suitable for administration to a patient body through a plurality of administration routes, including at least an oral administration route and a rectal administration route, without alteration of said physiologically acceptable formulation;
   wherein said single solid delivery form further comprises a dose delivery feature that allows said single solid delivery form to be adapted from delivery through one of said oral administration route and said rectal administration route to delivery through the other of said oral administration route and said rectal administration route; and
   wherein the dose delivery feature is adapted to result in absorption of substantially the same amount of said active pharmaceutical ingredient when the delivery form is administered through the oral administration route as when the delivery form is administered through the rectal administration route.

2. The composition of claim 1, wherein said oral administration route is selected from the group consisting of an oral transmucosal route and an oral gastrointestinal route.

3. The composition of claim 1, wherein said rectal administration route further comprises a rectal transmucosal route.

4. The composition of claim 1, wherein said solid delivery form is selected from the group consisting of a suppository, a lozenge, a swallowable tablet, a chewable tablet, and a dissolvable tablet.

5. The composition of claim 4 wherein said physiologically acceptable formulation further includes at least one additive selected from the group consisting of flavoring agents, coloring agents, sweetening agents, preservatives, adhesive-promoting agents, and glidants.

6. The composition of claim 4, wherein said active pharmaceutical ingredient is selected from the group consisting of analgesics, anti-allergy medications, anti-asthma medications, antibiotics, antiviral drugs, antifungal drugs, anticholinergics, anticonvulsants, antidepressants, antihistamines, antiemetics, antiseizure, antispasmodics, aminophylline, ascorbic acid, aspirin, acetaminophen, barbiturates, benzodiazepines, bisacodyl, butyrophenones, caffeine, chloral hydrate, chlorpromazine, clindamycin, clotrimazole, codeine, corticosteroids, dextromethorphan, diazepam, dinoprostone, diphenhydramine, ergotamine, estrogens, fentanyl, ferrous sulfate, guaifenesin, haloperidol, hormonal supplements, hydromorphone, indomethacin, kaolin, pectin, laxatives, lithium, loperamide, meclizine, meprobamate, methadone, metronidazole, miconazole, morphine, NSAIDS, opioids, orphenadrine, oxymorphone, pentobarbital, phenobarbital, phenothiazines, phenytoin, prochlorperazine, progestins, promethazine, ritalin, simethicone, spiramycin, sulfonamides, theophylline, trimethobenzamide, valproic acid, and vitamins.

7. The composition of claim 1, wherein said physiologically-acceptable formulation further includes a base component, and wherein said base component is selected from the group consisting of glycerinated gelatin, polyethylene glycol, and MBK fatty acid.

8. The composition of claim 1, further comprising at least one excipient ingredient.

9. The composition of claim 8, wherein said at least one excipient ingredient is selected from the group consisting of mannitol, dextrose, lactose, sucrose, and calcium carbonate.

10. The composition of claim 4, wherein said dose delivery feature of said delivery form further comprises a score mark disposed in a surface of said delivery form.

11. The composition of claim 10, wherein said score mark is disposed in said surface at a location reflective of the rate of absorption of said at least one active pharmaceutical ingredient in the oral cavity, gut, or rectum of said patient body.

12. The composition of claim 1, where a solid composition is enclosed in a capsule that can be swallowed or inserted rectally.

13. The composition of claim 10, wherein the score mark is disposed in a surface of said delivery form such that the delivery form is adapted to be broken along the score mark into a first portion and a second portion, the first portion being larger than the second portion.

14. The composition of claim 13, wherein administration of one of the first portion or the second portion via a rectal delivery route is adapted to result in absorption of substantially the same amount of said active pharmaceutical ingredient as would be absorbed when said delivery form is administered via an oral delivery route.

15. The composition of claim 13, wherein administration of one of the first portion or the second portion via an oral delivery route is adapted to result in absorption of substantially the same amount of said active pharmaceutical ingredient as would be absorbed when said delivery form is administered via a rectal delivery route.

16. A method of administering a composition to a patient, the method comprising:
providing a composition for administration to a patient body, the composition comprising a physiologically acceptable formulation including at least one active pharmaceutical ingredient, wherein said formulation including said at least one active pharmaceutical ingredient is provided in a single solid delivery form suitable for administration to a patient body through a plurality of administration routes, including at least an oral administration route and a rectal administration route, without alteration of said physiologically acceptable formulation, wherein said single solid delivery form further comprises a dose delivery feature that allows said single solid delivery form to be adapted from delivery through one of said oral administration route and said rectal administration route to delivery through the other of said oral administration route and said rectal administration route and wherein the dose delivery feature is adapted to result in absorption of substantially the same amount of said active pharmaceutical ingredient when the delivery form is administered through the oral administration route as when the delivery form is administered through the rectal administration route;
selecting one of said plurality of administration routes; and
delivering said composition in said delivery form to said patient via said selected one of said plurality of administration routes.

17. The method of claim 16, wherein said oral administration route is selected from the group consisting of an oral transmucosal route and an oral gastrointestinal route.

18. The method of claim 17, wherein said rectal administration route further comprises a rectal transmucosal route.

19. The method of claim 16, wherein said solid delivery form is selected from the group consisting of a suppository, a lozenge, a swallowable tablet, a chewable tablet, and a dissolvable tablet.

20. The method of claim 19, wherein said solid delivery form is a suppository, and said composition is administered via said rectal administration route.

21. The method of claim 19, wherein said solid delivery form is a suppository and further comprising adapting said delivery form to be administered via said oral administration route.

22. The method of claim 19, wherein said dose delivery feature of said solid delivery form further comprises a score mark disposed in a surface of said delivery form, the location of said score mark being reflective of the total dose delivered and the rate of absorption of said at least one pharmaceutical ingredient in said patient body.

23. The method of claim 22, further comprising administering said solid delivery form intact to one of said oral or said rectal administration routes.

24. The method of claim 23, further comprising breaking said solid delivery form along said score mark into first and second portions and administering either said first or said second portion to said patient body via the other of said oral and said rectal administration routes.

25. The method of claim 16, wherein said dose delivery feature of said delivery form further includes a score mark, and further comprising breaking said delivery form along said score mark into a first portion and a second portion, the first portion being larger than the second portion.

26. The method of claim 25, further comprising administering one of the first portion or the second portion via a rectal delivery route to cause absorption of an amount of active pharmaceutical ingredient that is substantially the same amount of the amount of said active pharmaceutical ingredient as would be absorbed when said delivery form is administered via an oral delivery route.

27. The method of claim 25, further comprising administering one of the first portion or the second portion via an oral delivery route to cause absorption of an amount of active pharmaceutical ingredient that is substantially the same amount of the amount of said active pharmaceutical ingredient as would be absorbed when said delivery form is administered via a rectal delivery route.

* * * * *

UNITED STATES PATENT AND TRADEMARK OFFICE
CERTIFICATE OF CORRECTION

| | | |
|---|---|---|
| PATENT NO. | : 8,157,788 B2 | Page 1 of 1 |
| APPLICATION NO. | : 10/702893 | |
| DATED | : April 17, 2012 | |
| INVENTOR(S) | : Gilbert R. Gonzales et al. | |

It is certified that error appears in the above-identified patent and that said Letters Patent is hereby corrected as shown below:

Column 4,
Line 24, "delivery" should be -- deliver --.

Signed and Sealed this
Third Day of July, 2012

David J. Kappos
*Director of the United States Patent and Trademark Office*